United States Patent [19]

Adler

[11] 3,991,705
[45] Nov. 16, 1976

[54] APPARATUS FOR PREPARING SMEARS OF BIOLOGICAL LIQUIDS

[75] Inventor: Stanford L. Adler, Monsey, N.Y.

[73] Assignee: Technicon Instruments Corporation, Tarrytown, N.Y.

[22] Filed: Nov. 4, 1974

[21] Appl. No.: 520,505

[52] U.S. Cl. .................................. 118/7; 118/257
[51] Int. Cl.² ........................................... B05C 1/14
[58] Field of Search .......... 118/257, 7, 259, DIG. 2, 118/DIG. 23; 23/253 R; 427/2, 4

[56] References Cited
UNITED STATES PATENTS

| | | | |
|---|---|---|---|
| 1,153,585 | 9/1915 | Vicars et al. | 118/257 X |
| 1,306,649 | 6/1919 | Weinheim | 118/257 X |
| 2,402,269 | 6/1946 | Alexander et al. | 118/65 X |
| 3,244,139 | 4/1966 | Brown et al. | 118/257 X |
| 3,418,053 | 12/1968 | Pelavin | 23/253 R X |
| 3,493,447 | 2/1970 | Rock | 156/57 |
| 3,526,536 | 9/1970 | Spengos et al. | 118/DIG. 2 |
| 3,701,337 | 10/1972 | Borelli et al. | 118/DIG. 23 |
| 3,716,019 | 2/1973 | Carter et al. | 118/259 X |

Primary Examiner—John P. McIntosh
Attorney, Agent, or Firm—S. P. Tedesco; Stephen E. Rockwell

[57] ABSTRACT

Apparatus and method for preparing a smear of a biological fluid substance on a substrate, utilizing a ribbon having relatively small openings in at least one surface thereof which openings are of substantially uniform size and are arranged substantially uniformly both longitudinally and transversely of the ribbon throughout at least a portion of the ribbon. The method includes the steps of supporting the substrate for movement and supporting the ribbon by a support in close proximity to the substrate at a substance-applying station, for a run of the ribbon past a portion of the substrate. Further steps include introducing a relatively small quantity of the aforementioned substance between the aforementioned ribbon surface portion and the substrate at the substance-applying station to spread by capillarity in a direction transversely of the ribbon, and moving the substrate in a direction to smear the substance on the substrate.

8 Claims, 5 Drawing Figures

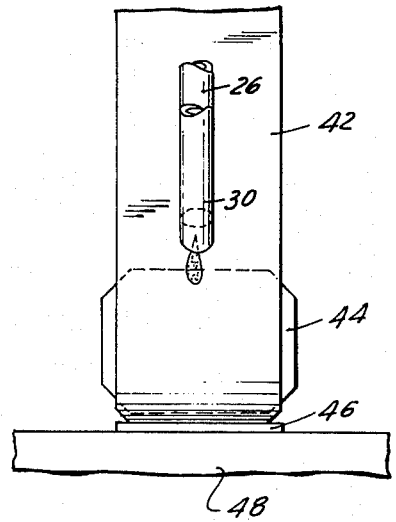
FIG. 3
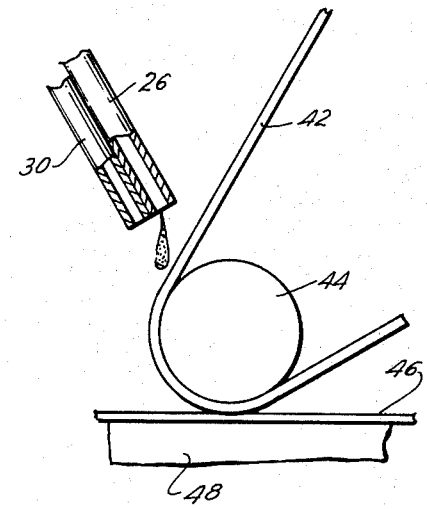
FIG. 2
FIG. 4
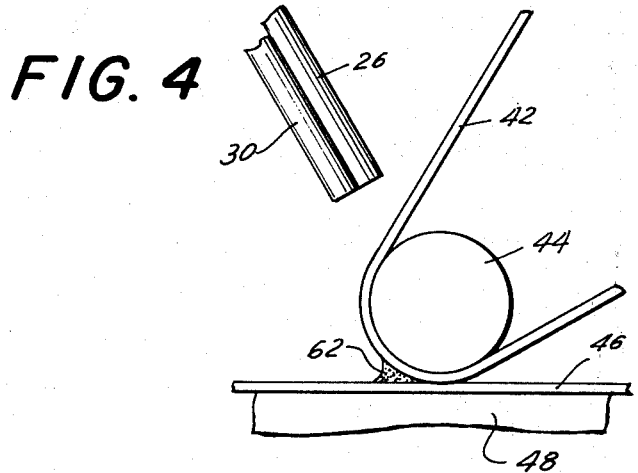
FIG. 5
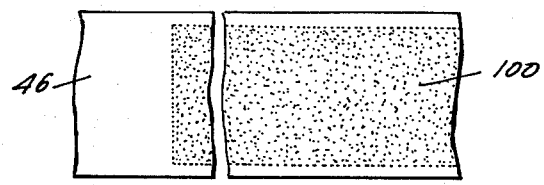

APPARATUS FOR PREPARING SMEARS OF BIOLOGICAL LIQUIDS

This application is a division of copending application Ser. No. 375,291, filed June 29, 1973, now U.S. Pat. No. 3,871,895.

BACKGROUND OF THE INVENTION

This invention relates to the preparation of biological

Prior Art

Heretofore smears of biological substances such as blood or cellular suspensions have been prepared for microscope examination by manipulation of microscope slides and slide cover slips. The technique requires a certain degree of expertise and, even with such skill, resulting smears have tended to lack uniformity and reproducibility. In the common manual preparation technique in which an end edge of an elongated slide is drawn lengthwise along a plastic strip or another such slide to smear a droplet of blood on the last-mentioned slide, the heavier cellular material tends very strongly to move out or away from the central longitudinal portion of the smear to be left on the smear in congregations along the sides of the smear. This is undesirable for microscopic cell examination. For such examination it is desirable that the cellular distribution be substantially even across the width of the smear throughout any given portion of the smear length. On the other hand, while it is desirable to have a mono-layer portion of cellular material available for such examination, it is also desirable to have available on a portion of the same smear a cellular gradient extending lengthwise of this smear and effecting some overlapping of cellular material in such region. Such smears having both types of layers permit differential cell counts under a microscope which counts are useful for diagnostic purposes, such as for malarial diseases for example.

It has been proposed that smears be prepared by a spinning process, and apparatus for carrying out such process has been commercially available. The process is one of centrifuging on a microscope slide a volume of biological fluid such as blood for a period sufficient to spread the specimen over a portion of the slide. It has been indicated in connection with such spinners that virtually the entire resulting smear has a mono-layer cellular distribution. This may be a drawback as previously indicated. Another drawback in such use of spinners is that an excess of a liquid specimen such as blood is spun off the slide to spray the environment such as ambient air and also splatter the inner wall surface of the spinner. Such blood specimens may carry infectious diseases, and hence the required cleanup operation of such spinners after use may be hazardous.

It is desired to obviate the aforementioned problems in the preparation of smears of biological substances. Moreover, it is desired to provide a method and apparatus for a preparation of such smears, which may be readily automated.

SUMMARY OF THE INVENTION

One object of the invention is to provide apparatus for preparing superior smears of biological substances for microscopic examination. Another object is to provide method and apparatus for preparing smears of the quality characterized above which is readily automated. Still aother object is to provide such technique and apparatus which has a further advantage that any excess of biological specimens not adhering to the substrate for the smear may be easily confined and collected for simple disposal and greater safety for users of the apparatus.

Further, there is provided apparatus for preparing a smear of a biological fluid substance on a substrate, utilizing a ribbon having relatively small openings in at least one surface thereof which openings are of substantially uniform size and are arranged substantially uniformly both longitudinally and transversely of the ribbon throughout at least a portion of the ribbon. The method contemplates the steps of supporting the substrate for movement and supporting the ribbon by a support in close proximity to the substrate at a substance-applying station, for a run of the ribbon past a portion of the substrate. It further contemplates in combination the steps of introducing a relatively small quantity of the aforementioned substance between the aforementioned ribbon surface and the substrate at the substance-applying station to spread by capillarity in a direction transversely of the ribbon, and moving the substrate in a direction to smear the substance on the substrate.

BRIEF DESCRIPTION OF THE DRAWINGS

FIG. 2 is an enlarged fragmentary elevational view illustrating the substance-applying station of the apparatus;

FIG. 3 is a view similar to FIG. 2 taken on line 3—3 of FIG. 2;

FIG. 4 is a view similar to FIG. 3 but showing a later step in the operation of the apparatus; and FIG. 5 is a fragmentary, broken plan view illustrating a smear prepared in accordance with the invention on a substrate therefor.

DETAILED DESCRIPTION OF THE PREFERRED EMBODIMENT

Figure 1:
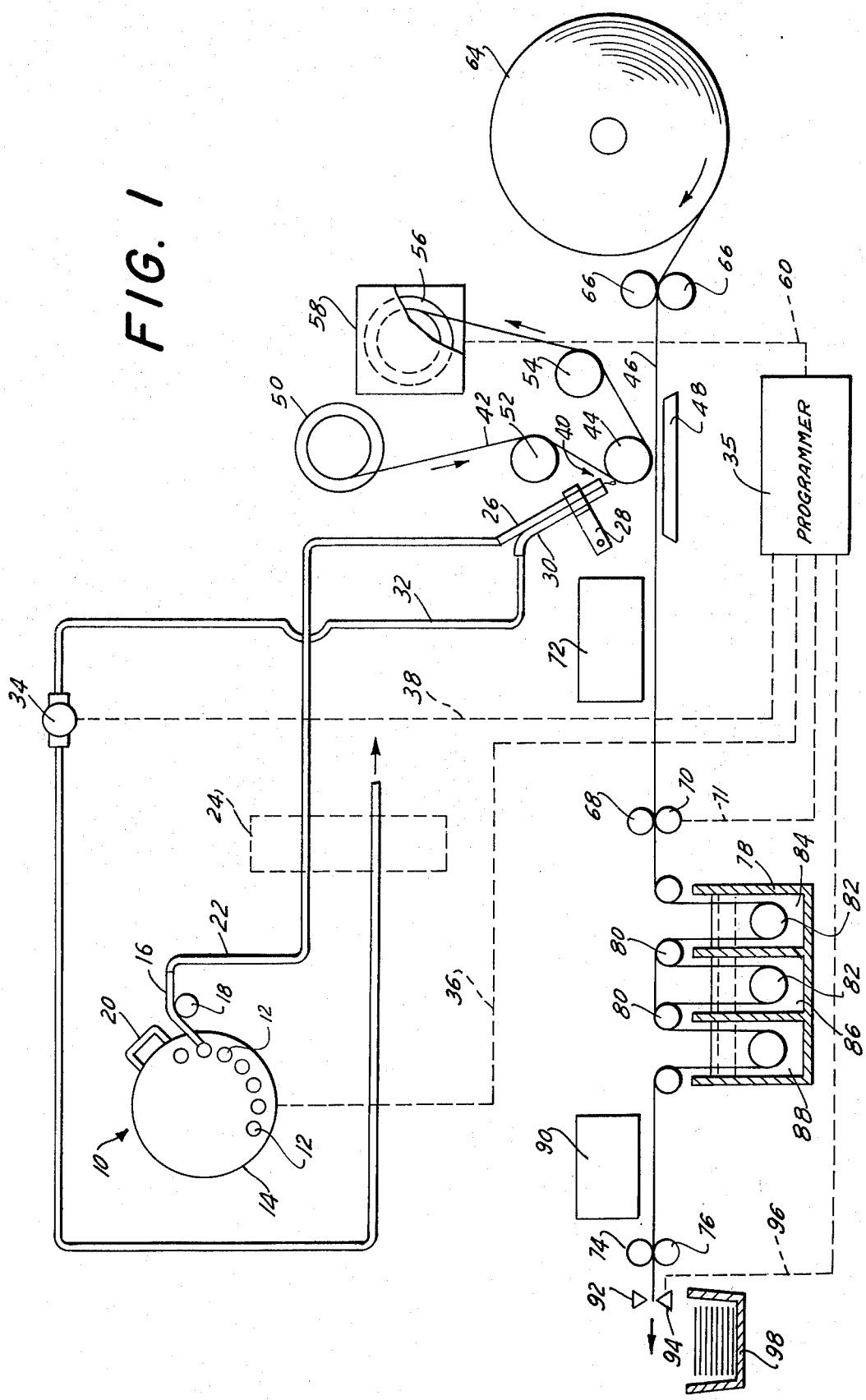
FIG. 1 is a schematic view of apparatus for the preparation and treatment of smears of biological liquids or suspensions on a substrate and embodying the invention.

In FIG. 1 of the drawings, there is shown a source 10 of biological fluid samples. The samples may be a series of different discrete blood samples, each of which samples being separately supported and confined in a cup 12 of a series of cups supported on a motor-driven turntable 14 of a sampler. Associated with the sampler is a conventional movable probe 16 provided on support 18 for movement of the probe into the cup then indexed therewith for aspiration of the sample and then into the liquid within a wash receptacle 20 for aspiration of the wash liquid before the probe 16 enters the next sample cup after movement of the turntable 14. Between immersions in sample and wash liquid, the probe 16 aspirates air and the resultant sample stream flowing from the probe 16 is segmented by segments of air and wash liquid which segmentation of the sample stream preserves the integrity of the different samples, all of which is conventional in continuous-flow wet-chemical analysis equipment of the automated type. The segmented stream flowing from the probe 16 is conveyed therefrom through the coupled inlet end of a compressible pump tube 22 under the action of a pump 24 which may be of a conventional peristaltic type. The pump tube 22 has the outlet end thereof connected to the inlet end of a metal tube 26 of cannula size having a free outlet end and provided with a stationary support as by a bracket 28. In general parallelism with metal tube 26 is a similar tube 30 having an inlet end along side and preferably flush with the outlet end of the tube 26 as shown. To the outlet end of the tube 30 is connected the inlet end of a compressible pump tube 32 which tube extends through a pinch valve 34 which is electrically operated. The compressible tube 32 extends from the valve 34 through the pump 24. The construction and arrangement is such that when the pinch valve 34 is open the sample stream discharged by the tube 26 flows into the tube 30 for flow through the pump 24 for disposal as to waste or, if desired, to some other analysis station (not shown) for an additional and different type of analysis of each sample. The tube 26 is washed between samples by the wash segments of the stream.

The operation of the motor-driven turntable 14 and the movements of the probe 16 associated with the sampler are controlled as shown from a programmer 35 through a lead 36, and the operation of the valve 34 is controlled from the programmer 36 through a lead 38. The control of the valve 34 is such that, for a time period during the flow of each sample from the tube 26, the valve 34 is closed so that there is no aspiration through the tube 30 and a volume of the liquid specimen drops by gravity from the discharge end of the tube 26 at the substance-applying station of the apparatus, designated generally at 40. The aspirated volume of each sample may be of the order of approximately 160 microliters, and the volume of sample dispensed at the substance-applying station 40 to fall freely from the discharge end of the tube 26 may be of the order of approximately 27 microliters. This dispensed volume may be in the form of a droplet of blood.

The dispensed volume of sample falls on a ribbon 42, the volume falling in the illustrated form on a portion of the ribbon 42 backed by a platen 44. In the illustrated form the platen 44, which has an arcuate surface over which the ribbon 42 runs when driven, is mounted in fixed position by a suitable support not shown. The platen 44 may be structured as best shown in FIGS. 2 and 3 so that the greater part thereof is of cylindrical form. The platen may take the form of a stationary rod. The portion of the ribbon 42 backed by the platen 44 cooperates with a substrate to receive the biological smear, which substrate is shown as being continuous and is structured of a tape 46 which lies in a path over a tape support 48 below the platen 44.

The ribbon 42 is supplied from a suitably supported supply spool 50 and is guided, when driven, by guides 52 and 54. A motor-driven take-up spool 56 is provided for the ribbon 42 and the spool is preferably housed in a box cover 58 and is disposable therewith to very effectively inhibit contamination to the user by an infectious disease which may be carried by that portion of each blood specimen remaining on the ribbon 42 after the preparation of smears from those samples. The driving motor of the spool 56 is controlled by a lead 60 from the programmer 35.

The preferred operation of the apparatus is such that after the deposit on the ribbon 42, while the pinch valve 34 is open and the tape 46 is stationary, the ribbon 42 is driven a distance sufficient to carry the sample, which may have some flow on the ribbon, to a position extending between the ribbon 42 and the tape 46 as shown in FIG. 4. The ribbon 42 carrying the sample preferably has contact with the tape 46 although if relatively thick smears are desired the ribbon 42 may be out of contact with the tape 46.

The ribbon 42, having a thickness of approximately 0.002 inch, may be structured of metal but it has been found more convenient and less expensive to form it of non-metallic fibers which may be woven or non-woven. At present, a ribbon woven of nylon fibers has been found to be more than adequate for the purpose with the warp and weft fibers thereof forming interstices in the ribbon of approximately 50 by 50 microns. Where the substrate tape 46 is approximately five-eighths inch in width the nylon ribbon may be approximately one-half inch in width, the length of the cylindrical portion of the platen 44 being somewhat less than the width of the ribbon. The ribbon overlaps portions of tapered ends (FIG. 3) of the platen 44. By way of example only: the platen may have a diameter of approximately three-eighths inch, if cylindrical. If the ribbon 42 having the aforementioned interstices therein is not woven, for example, or is of a limited structure, it is important that at least the surface of the ribbon 42 which receives the sample thereon have openings in the last-mentioned surface of approximately the same size as the aforementiond interstices, which if they are not through holes, at least provide relatively small recesses or pockets, hereinafter referred to as openings, in the last-mentioned surface of the ribbon 42 for a purpose which will be made clear hereinafter. Such openings may be provided by a textured ribbon surface. These through or blind openings in the ribbon 42 should be evenly distributed across the ribbon and have the same spacing with reference to one another in their arrangement lengthwise of the ribbon 42 at least in each region of the surface on which each sample portion is introduced.

It is believed made clear from the foregoing that advancement of the ribbon introduces the previously dispensed sample portion to a position to extend between the ribbon 42 and the substrate 46 as shown at 62 in FIG. 4. The application of the sample portion to the substrate tape 46 is facilitated by the capillary spreading action of the sample portion transversely of the ribbon 42. The sample portion also spreads on the ribbon 42 during this period lengthwise of the tape. During this flow or spreading action on the ribbon 42 of the liquid sample or suspension, any cellular material such as blood cells of a blood specimen flow in the same direction.

When the advance of the ribbon 42 has terminated, and while the sample stream discharged by the dispensing tube 26 is conveyed to the tube 30 to the tube 34 through which the stream is conveyed through the open valve 34, the tape substrate 46 is advanced on the tape support 48 in the direction of the arrow causing the biological substance extending between the ribbon 42 and the substrate tape 46 to be smeared on the latter lengthwise thereof. As the substrate tape 46 moves below the ribbon surface having through or blind openings therein, the boundaries of the openings tend to retard the displacement of heavier cellular material transversely of the substrate tape 46, which otherwise would have an irregular and non-uniform disposition on the substrate tape 46. The substrate tape may be conveniently supplied from a supply roll 64 and passed between a pair of guide rolls 66 prior to passage over the tape support 48 which, in the illustrated form, is shown as being horizontally arranged. Rolls 68 and 70 cooperate with one another and with the substrate tape passing therebetween. The roll 70 is driven by a motor, not shown, controlled from the programmer 35 through a lead 71. The rolls 68 and 70 have only edge contact with the substrate tape 46 so as to avoid contact with the smear on the tape 46.

In the illustrated form, during advancement of the tape substrate 46 by the aforementioned drive, a smear approximately 5½ inches long is made on the substrate tape 46 prior to running dry under the ribbon-supporting platen 44. Travel of the tape is discontinued in this form after another approximately one-half inch of travel of the substrate tape so that the smear is followed by a clean portion of the tape. In this manner this smear and the smear next to follow are separated on the substrate tape 46.

It will be evident that the smear prepared in the aforementioned manner has a cellular gradient extending length-wise of the smear which gradient is less in the direction to the right of the apparatus as viewed in FIG. 1. Because of the substantially uniform cell distribution of the specimen transversely of the ribbon 42 at the substance-applying station 40 any particular transverse section of the smear has substantially uniform transverse cellular distribution. As the smear has the aforementioned gradient lengthwise thereof, the smear has a plural layer of cellular material throughout a portion thereof and also has a portion thereof coated with a monolayer of cellular material. Such a smear may have at least five times the useful area for microscopic examination as conventional slides prepared manually. The tape under the action of the drive roll 70 travels a distance of approximately 6 inches in the illustrated form. The travel of the tape past the substance-applying station 40 terminates under the control of the programmer 35 as aforesaid. The programmer 35 then initiates and later terminates through lead 60 a second advance of the ribbon 42 to bring a second portion thereof below the outlet of the sample discharge tube 26 and the apparatus is then in condition to commence the next cycle of operation to prepare a similar smear on substrate tape 46 of a portion of the next following sample, under the control of the programmer 35.

As the substrate tape 46 is periodically advanced in this manner the first such smear on the substrate tape 46 passes under a dryer 72 of a blower type which dries such smear on the tape 46. Spaced to the left of the tape rolls 68 and 70 as viewed in FIG. 1 are tape rolls 74 and 76 cooperating with one another and with the tape 46 therebetween. The roll 76 may be driven continuously but at a much slower driving rate than the previously described roll 70. Intermediate the rolls 68, 70 and the rolls 74, 76 the tape 46 carrying such smears thereon is passed through the compartments of a container 78. As indicated in FIG. 1 the compartments of container 78 may be three in number and each compartment is filled with a liquid which is isolated therein. As indicated in FIG. 1, the tape is guided sequentially through the compartments through a series of guide rollers, certain of such rollers being indicated at 80 and others being indicated at 82.

The substrate tape may be formed conveniently of a plastic material such as Mylar. Acetate is the preferred material for the substrate tape 46. The tape 46 carrying such smears of different blood specimens, for example, may be coded (not shown) in any conventional manner to identify the source of each blood specimen. Such tape carrying such blood smears and issuing from the rolls 68, 70 passes first into a staining solution in compartment 84 of the container 78. Such tape then passes to compartment 86 containing buffer solution which, like the solution of the staining bath, is a conventional solution. From the compartment 86 the tape then travels into compartment 88 containing a wash solution for the blood smears. The substrate tape then passes under a dryer 90 of the blower type to dry the substrate tape carrying such smears, prior to entry of the tape 46 between the rolls 74 and 76.

The portions of the tape 46 carrying the smears one such smear (FIG. 5) being indicated at 100, issue sequentially from between the rolls 74 and 76 and pass under an anvil 92 with which a solenoid-operated movable cutter element 94 cooperates to sever these tape portions from each other, each with a complete blood smear thereon. The solenoid-operated cutter element 94 is operated from the programmer 35 through lead 96. The severed tape portions bearing the respective blood smears may be collected in any suitable fashion. In the illustrated form, the severed tape portions fall by gravity for vertical stacking in a bin-like receptacle 98. The tape-carried treated smears may be stacked at a rate of about one a minute which production rate substantially exceeds that of any other known process of preparing and treating biological smears.

For microscopic examination of such treated biological smears on an acetate film substrate, the film is placed on a microscope slide with the smear side down and the treated smear with optical immersion oil between the smear and the slide. No glass cover slip is required, and this facilitates the assembly of the smear carrying film with the slide for microscopic examination. If Mylar film is used instead of acetate film as a substrate, a cover slip is required as Mylar has birefractive properties. If Mylar film is used as a substrate, the film is placed with the smear side up on a glass slide with optical immersion oil between the film and the slide. A cover slip is placed over the smear with optical immersion oil between it and the smear.

Among other advantages of smears prepared in accordance with the invention is the high degree of reproducibility of smears of the same specimen, say a blood specimen, under similar operating conditions such as temperature and viscocity of the specimen. There is also a high degree of uniformity between the character of smears from different blood specimens.

While the presently preferred embodiments of apparatus and method for preparing smears of a biological substance on a substrate have been illustrated and described, it will be apparent, especially to those versed in the art, that the apparatus and method may take other forms and are susceptible in various changes in details without departing from the principles of the invention.

What is claimed is:

1. Apparatus for preparing a smear of a biological liquid, comprising: a movable first element having a surface extending in a first direction, a movable second element having a second surface, said surfaces being adapted to have portions thereof in opposing relation, means for locating said surface portions of said elements in at least close proximity, means for introducing at one time a predetermined discrete volume of the biological liquid between said surface portions which are in at least close proximity, positive means to move each of said elements, control means for actuating and positive means for said second element relatively to said first element to present said surface portion of said second element in said opposing relation to the surface portion of said first element, and said control means actuating said positive means for moving said first element a limited distance, so as to wipe a smear of said biological liquid on a limited area of one of said elements.

2. Apparatus as defined in claim 1, wherein: said first element is structured as a tape.

3. An apparatus as defined in claim 2, wherein: said biological liquid is one of a series of samples of such liquid, said means for introducing said liquid introducing said samples periodically for sequential introduction of said samples, and said positive means for moving said first element moving said first element periodically for forming a series of spaced smears on said surface of said first element.

4. Apparatus as defined in claim 2, wherein: said second element which is moved to present said surface portion thereof is structured as a ribbon, and said smear is formed on said tape.

5. Apparatus as defined in claim 4, wherein: said ribbon element has means defining relatively small openings in at least a portion of the surface thereof exposed to the sample, said openings being of substantially uniform size and being arranged substantially uniformly both longitudinally and transversely of the ribbon element through said ribbon portion.

6. Apparatus as defined in claim 1, wherein said means for locating said surface portions comprises means locating said surfaces in contact with one another.

7. Apparatus as defined in claim 1, wherein: said second element comprises a ribbon element, said means introducing the biological liquid including said positive means moving said ribbon element.

8. Apparatus as defined in claim 7, wherein: said means for locating said ribbon surface portion comprises a platen having an arcuate surface portion opposing said surface portion of said first element.

* * * * *

UNITED STATES PATENT AND TRADEMARK OFFICE
CERTIFICATE OF CORRECTION

PATENT NO. : 3,991,705
DATED : November 16, 1976
INVENTOR(S) : Stanford L. Adler It is certified that error appears in the above-identified patent and that said Letters Patent are hereby corrected as shown below:

Column 6, line 66, "and" should read -- said --.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*